United States Patent [19]

Mattei

[11] 4,185,637

[45] Jan. 29, 1980

[54] COATING COMPOSITION FOR SUTURES

[75] Inventor: Frank V. Mattei, Piscataway, N.J.

[73] Assignee: Ethicon, Inc., Somerville, N.J.

[21] Appl. No.: 910,263

[22] Filed: May 30, 1978

[51] Int. Cl.$^2$ .............................................. A61L 17/00
[52] U.S. Cl. ............................ 128/335.5; 427/434 D; 427/2; 428/378
[58] Field of Search ................ 128/335.5, 326, 334 R, 128/335; 428/375, 377, 378; 427/2, 434 D

[56] References Cited

U.S. PATENT DOCUMENTS

| | | | |
|---|---|---|---|
| 3,297,033 | 1/1967 | Schmitt et al. ................ | 128/335.5 |
| 3,527,650 | 9/1970 | Block ............................ | 128/335.5 |
| 3,565,869 | 2/1971 | De Prospero ................. | 260/78.3 |
| 3,636,956 | 1/1972 | Schneider ..................... | 128/335.5 |
| 3,810,784 | 5/1974 | Wong et al. .................. | 428/378 |
| 3,942,532 | 3/1976 | Hunter et al. ................ | 128/335.5 |
| 4,027,676 | 6/1977 | Mattei .......................... | 128/335.5 |
| 4,074,005 | 2/1978 | Moore et al. ................. | 428/378 |
| 4,076,798 | 2/1978 | Casey et al. .................. | 128/335.5 |
| 4,105,034 | 8/1978 | Shalaby et al. ............... | 128/335.5 |

*Primary Examiner*—Robert W. Michell
*Assistant Examiner*—C. F. Rosenbaum
*Attorney, Agent, or Firm*—Wayne R. Eberhardt

[57] ABSTRACT

The tie-down properties of multifilament surgical sutures are improved by coating the suture with a composition comprising a gel of a fatty acid salt in a volatile organic solvent. The gel is prepared by refluxing the fatty acid salt in the organic solvent. Sutures coated with the gel are dried to remove the solvent and deposit a residue of the fatty acid salt on the suture. Sutures coated with from 1 to 5 percent by weight of the dry fatty acid salt are characterized by a smooth knot tie-down under both wet and dry conditions.

20 Claims, No Drawings

COATING COMPOSITION FOR SUTURES

BACKGROUND OF THE INVENTION

1. Field of the Invention

This invention relates to a composition useful as a coating and lubricating finish for surgical sutures. More particularly, this invention relates to a means for improving the tie-down properties of multifilament, absorbable sutures by coating the sutures with a single-component, absorbable composition comprising a fatty acid salt applied to the suture from a gel of the salt in a volatile organic solvent.

2. Description of Prior Art

Suture materials are generally classified as either absorbable or nonabsorbable, with each type of suture material being preferred for certain applications. Absorbable suture materials are preferred for internal wound repair in which the sewn tissues will hold together after healing without suture reinforcement and in which a nonabsorbed suture may promote tissue irritation or other adverse bodily reaction over an extended period of time. Suture materials are considered to be absorbable if they disappear from the sewn tissue within about a year after surgery, but many absorbable suture materials disappear within shorter periods.

The earliest available absorbable suture materials were catgut and extruded collagenous materials. More recently, absorbable sutures derived from synthetic polymers have been developed which are strong, dimensionally uniform, and storage-stable in the dry state. Typical of such polymers are lactide homopolymers, and copolymers of lactide and glycolide such as those disclosed in U.S. Pat. No. 3,636,956, and glycolide homopolymers such as those disclosed in U.S. Pat. No. 3,565,869, both patents being incorporated herein by reference.

Monofilament synthetic absorbable suture materials are generally stiffer than their catgut or collagen counterparts, and synthetic absorbable sutures are therefore usually employed in a multifilament, braided construction in order to provide the suture with the desired degree of softness and flexibility. Such multifilament sutures often exhibit a certain degree of undesirable roughness or "grabbiness" in what has been termed their "tie-down" performance, i.e., the ease or difficulty of sliding a knot down the suture into place.

Multifilament nonabsorbable sutures such as braided sutures of polyethylene terephthalate, for example, can be improved with respect to tie-down performance by coating the external surface of the suture with solid particles of polytetrafluoroethylene and a binder resin as disclosed in U.S. Pat. No. 3,527,650. This procedure, however, is undesirable as applied to absorbable sutures because polytetrafluoroethylene is nonabsorbable and sutures coated therewith would leave a particulate residue in the sewn tissue after the suture had absorbed.

Multifilament, nonabsorbable sutures can also be improved with respect to tie-down performance by coating them with a linear polyester having a molecular weight between about 1,000 and about 15,000 and at least two carbon atoms between the ester linkages in the polymer chain as disclosed in U.S. Pat. No. 3,942,532. This patent discloses that the aforementioned polyesters may also be used to coat absorbable synthetic sutures, but does not consider that such coated sutures would not be totally absorbable.

U.S. Pat. No. 3,297,033 discloses that absorbable polyglycolic acid sutures may be coated with conventional suture coating materials such as a silicone or beeswax in order to modify the handling or absorption rate of the sutures. These coating materials are not readily absorbable, however, and will accordingly leave an undesirable residue in the tissue after the suture itself is absorbed.

An absorbable, three-component composition for coating absorbable sutures is described in my earlier patent, U.S. Pat. No. 4,027,676. This coating comprises a combination of a film-forming polymer such as a lactide or glycolide homopolymer or copolymer, a lubricant which is preferably a polyalkylene glycol, and a hydrophobic component which is preferably a higher fatty acid or ester. While this composition gives good results, it requires the formulation of a multicomponent system, and is accordingly less convenient to use than the single-component coating composition of the present invention.

It is accordingly an object of the present invention to provide an absorbable, lubricating coating for multifilament sutures of braided, twisted or covered construction. It is a further object of this invention to provide an absorbable coating to improve the tie-down properties of such multifilament sutures. It is a yet further object of this invention to provide a single-component composition useful as a coating to improve the tie-down properties of absorbable, multifilament sutures.

SUMMARY OF THE INVENTION

In accordance with the instant invention, there is provided as a coating for sutures, particularly synthetic absorbable multifilament sutures, an absorbable composition comprising a gel of a polyvalent metal ion salt of a $C_6$ or higher fatty acid in a volatile organic solvent. The composition is prepared by refluxing a dispersion of the fatty acid salt in the organic solvent. The gel is applied directly to the suture and the solvent removed by drying to provide a final coating add-on of from about 1 to 5 percent residual fatty acid salt by weight of the dry suture.

The fatty acid salt is preferably a calcium salt of a $C_6$ to $C_{22}$ fatty acid, and the organic solvent is preferably one of the benzene series. The solids content of the gelled composition is generally in the range of 5 to 10 percent. The coating is absorbable in animal tissue and the method of the invention is particularly useful for improving the tie-down smoothness of braided sutures prepared from poly(p-dioxanone) or other absorbable polymers.

DESCRIPTION OF PREFERRED EMBODIMENT

The coating compositions of the instant invention may be applied to any suture material where it is desired to improve fiber lubricity, suture tie-down characteristics, or the like. The coating is particularly useful with synthetic absorbable multifilament sutures composed of polylactide, polyglycolide, copolymers of lactide and glycolide, poly(p-dioxanone), poly(alkylene oxalate), and mixtures of such polymers with each other and with other compatible absorbable compositions as those described, for example, in U.S. Pat. Nos. 4,052,988; 3,636,952; and 2,683,136, which patents are incorporated herein by reference.

The coating compositions of the present invention are gels of higher fatty acid salts which are prepared by refluxing a dispersion of the salt in a volatile organic solvent. Useful fatty acid salts are the polyvalent metal ion salts of the $C_6$ and higher fatty acids, particularly those having from about 12 to 22 carbon atoms, and mixtures thereof. Illustrative of such salts are the calcium, magnesium, barium, aluminum and zinc salts of stearic, palmitic and oleic acids. Particularly preferred is commercial "food grade" calcium stearate which consists of a mixture of about one-third $C_{16}$ and two-thirds $C_{18}$ fatty acids, with small amounts of the $C_{14}$ and $C_{22}$ fatty acids.

Volatile organic solvents useful in preparing gels of the fatty acid salts are actually nonsolvents for the salts and include both aromatic and aliphatic hydrocarbons having boiling points between about 50° and 180° C. Illustrative of useful solvents are the aromatic series of benzene, toluene, xylene, and mesitylene, and the aliphatic solvents, 1,1,2-trichloroethane and chloroform.

The gelled, fatty acid salt is prepared by refluxing a dispersion of from about 1 to 5 percent of the selected salt or mixture of salts in a selected solvent under atmospheric pressure and for the time necessary to allow for complete gelation of the mixture. The fatty acid salt is preferably reduced to a fine powder before mixing with the solvent to facilitate dispersion and subsequent gelation. The mixture is then stirred to disperse the fatty acid salt and heat is applied. Initial gelation may be observed at temperatures below reflux, but heating is preferably continued with rapid agitation until reflux is attained. After maintaining reflux temperatures for about 1 to 5 hours, the gel is allowed to cool to room temperature with continuous, vigorous stirring. Eventually, the gel structure breaks down to a dispersion of small gel particles in excess solvent. The gel is separated from excess solvent by decantation/filtration and appears as a compact, gelatinous, translucent mass of from about 3 to 10 percent solids.

The gelled fatty acid salt is conveniently applied to the suture by passing the suture through a container of the gel and wiping excess gel from the suture as it exits the container. Other conventional methods of applying coatings or finishes to continuous strands of fibers may also be used with equally good results. The coated suture is air and vacuum dried to remove the organic solvent from the gel and thereby obtain the finished, coated product. Preferably, the application of gel to the suture is regulated to provide from about 1 to 5 percent dry coating by weight of the suture.

Sutures coated in accordance with the present invention are characterized by improved wet and dry tie-down properties as compared to uncoated sutures. The coating adheres well to the suture and is translucent so that the appearance of the coated suture is not significantly altered by the coating and there is no appreciable dusting or flaking of the coating during tie-down. In contradistinction thereto, I have found that sutures coated with a dispersion of ungelled, fatty acid salt in an organic solvent have a definite whitish appearance and dust or flake significantly during tie-down, and are consequently considered to be unsatisfactory by many surgeons. The gelled fatty acid salts of the present invention are accordingly much preferred over the ungelled salts as a suture coating composition.

In coating multifilament sutures with the gelled fatty acid salt in accordance with the present invention, it is not necessary that every filament within the suture be individually or completely coated. In most instances, the coating will penetrate at least partially into the interstices of the suture, but it is only important that the outer surface be well covered in order to reduce frictional forces during suture tie-down.

The amount of coating composition applied to the fiber, or the coating add-on, will vary depending upon the construction of the fiber, e.g., the number of filaments and tightness of braid or twist, and the nature of the coating material, e.g., the viscosity and consistency of the gel. In general, the coating composition applied to a braid will constitute from about 1 to about 5 percent by weight of the dry, coated fiber, but coating composition add-on may range from as little as about 0.5 percent by weight to as much as about 10 percent or higher in some cases. As a practical matter, and for reasons of economy and general performance, it is preferred to apply the minimum amount of coating composition consistent with good tie-down performance, and this level of add-on is readily determined experimentally for any particular fiber-coating system and is usually within the range of 2 to 4 percent by weight.

The improvement in tie-down properties imparted to synthetic absorbable sutures may be determined semi-quantitatively by comparing the feel of coated and uncoated sutures during the act of tying down a single throw knot. Such comparisons are made on both wet and dry sutures since many suture coatings result in different tie-down properties when tested wet or dry. Suture tie-down roughness is graded from 0 to 10 with 0 being comparable to an uncoated suture and 10 indicating no detectable roughness.

Suture tie-down properties are evaluated dry after the sutures have been conditioned for at least 2 days in a vacuum drying oven at room temperature and 100 microns or less absolute pressure, and wet after being immersed in water at 25° C. for 1 minute. Roughness values above 4 are considered acceptable, while values of 7 or higher are comparable to conventional silicon-coated silk and are considered fully satisfactory.

EXAMPLE I

Twenty-four grams of calcium stearate (food grade) and 1176 g of xylene (reagent grade mixed isomers) were slurried in a round bottom flask equipped with mechanical stirring, reflux condenser and thermometer. Heat was applied slowly with rapid stirring. At 100° C., the dispersion formed an opaque, almost immobile gelatinous mass; at 115° C., the mass congealed into an immobile translucent mass. Heating was continued with maximum stirring to reflux at 138° C., and reflux conditions were maintained for 4 hours. The gelatinous mass was thereafter allowed to cool slowly with continued vigorous stirring. At 90° C., the gel clarified completely; at 80° C., inversion from a gel to a quasi-sol began; at 75° C., the gel structure had disintegrated to a dispersion of gel particles in excess solvent. The gel was separated from the excess solvent by decantation and filtration. The gel mass was translucent and contained about 10 percent solids.

An absorbable, braided size 0 suture composed of poly(p-dioxanone) was passed through the gel mass at a rate of about 10 feet per minute. Folded pads of soft felt were positioned to gently encircle the braid as it exited the gel in order to wipe off excess coating and assure uniformity of application. The coated braid was dried with high velocity, filtered air followed by vacuum drying, and residual xylene content was below detectable limits of 0.4 ppm. The level of coating was determined to be 2.26 percent by weight on the dry suture. The coated suture was sterilized with ethylene oxide using conventional procedures. The final suture strand had a clean, uniform appearance with excellent wet and dry tie-down ratings of 9 to 10 respectively. The suture evidenced no significant dusting or flaking of the coating during tie-down.

Repetition of the experiment with coating levels of 1.9 to 2.9 percent by weight and with size 2-0 braided suture of poly(p-dioxanone) produced similar results.

Repetition of the experiment with a coating level of 1.4 percent by weight on a size 2-0 braided suture composed of a 90/10 glycolide/lactide copolymer resulted in a similar improvement in wet and dry suture tie-down characteristics.

EXAMPLE II

The calcium stearate gel of Example I was diluted from 10 percent to 6 percent solids with additional xylene to obtain a composition having marginally flowable characteristics. Braided, size 2-0 90/10 glycolide/lactide suture was coated with the diluted gel according to the procedure of Example I to provide a coating add-on of 1.6 percent by weight. The coated suture exhibited improved wet and dry tie-down characteristics similar to those obtained in Example I.

EXAMPLE III

Braided sutures coated with calcium stearate gels prepared according to the general method of Example I using benzene, toluene, o-xylene, mesitylene, 1,1,2-trichloroethane and chloroform as the organic solvents exhibit similar improvement in wet and dry tie-down characteristics.

EXAMPLE IV

A calcium stearate gel was prepared according to the method of Example I with a "substantially carbonate free" grade of calcium stearate. The resulting gel was visually more transparent than the gel of Example I, demonstrating that the normal translucent quality of the gel is due at least in part to the presence of insoluble, nongelling carbonates. A braided suture coated with the gel had an excellent appearance and demonstrated similarly improved wet and dry tie-down characteristics.

EXAMPLE V

The braided suture of Example I was coated with a dispersion of 20 percent calcium stearate in xylene prepared in a ball-mill. The dry, coated suture demonstrated significantly improved wet and dry tie-down, but dusted badly during dry tie-down.

While the foregoing description and examples have been directed to coating absorbable multifilament braided sutures, it will be readily appreciated that the coating may likewise be applied, if desired, to absorbable monofilament sutures as well as on nonabsorbable monofilament and multifilament sutures.

Nonabsorbable sutures such as cotton, linen, silk, nylon, polyethylene terephthalate and polyolefins are normally coated with nonabsorbable compositions. Polyolefins are usually of monofilament construction while cotton, linen, silk and polyester are usually of braided or twisted multifilament construction. While there is usually no requirement that the coating on such sutures be absorbable, the composition of the instant invention may, nevertheless, be used as a lubricating finish for all these sutures if desired.

The coating composition may, if desired, also contain components other than those discussed above for other useful purposes including dyes, antibiotics, antiseptics, anesthetics and anti-inflammatory agents.

In the above examples, the coating was applied to the braided suture strand in order to provide a substantially continuous coating on at least the outward-facing surfaces of the outer-most filaments of the braid. It is understood, however, that the coating may be applied, if desired, to individual filaments before they are formed into strands or to individual strands before they are processed into the final suture structure. Also, while the above examples were conducted with size 0 or 2-0 braided suture, this was for the sake of convenience only, and the invention is not so limited as to suture size or construction, but may be practiced, for example, with sutures from size 10-0 to size 2 and larger which may be twisted, covered, or of other multifilament construction. The foregoing examples are intended to be merely illustrative, and many modifications and variations thereof will be apparent to those skilled in the art.

What is claimed is:

1. A multifilament suture having improved tie-down properties, said suture being coated with from about 1 to 5 percent by weight of the dry residue of a composition comprising a gel of a polyvalent metal ion salt of a $C_6$ or higher fatty acid in a volatile organic solvent.

2. A suture of claim 1 wherein the fatty acid salt is the salt of calcium, magnesium, barium, aluminum, or zinc.

3. A suture of claim 1 wherein said higher fatty acid is selected from the group consisting of $C_{12}$ to $C_{22}$ fatty acids and mixtures thereof.

4. A suture of claim 3 wherein the fatty acid salt is the salt of calcium or magnesium.

5. A suture of claim 4 wherein the fatty acid comprises a mixture of stearic and palmitic acid.

6. A suture of claim 1 wherein the fatty acid salt is calcium stearate.

7. A suture of claim 6 wherein the calcium stearate salt is substantially free of carbonates.

8. A suture of claim 1 wherein said gel contains from about 3 to 10 percent solids and is obtained by refluxing the fatty acid salt in the volatile organic solvent.

9. A suture of claim 1 wherein said volatile organic solvent is selected from the group consisting of benzene, toluene, xylene, mesitylene, 1,1,2-trichloroethane, and chloroform.

10. A suture of claim 1 wherein the suture is comprised of homopolymers or copolymers of lactide and glycolide.

11. A suture of claim 1 wherein the suture is composed of poly(p-dioxanone).

12. A suture of claim 1 wherein the multifilament suture is a braided suture.

13. A method for improving the tie-down properties of a multifilament suture which comprises
    coating the suture with a composition comprising a gel of a polyvalent metal ion salt of a $C_6$ or higher fatty acid in a volatile organic solvent, and
    drying said coated suture to remove the organic solvent from said gel and deposit on the suture from about 1 to 5 percent by dry weight of the fatty acid salt.

14. A method of claim 13 wherein the gel contains from about 3 to 10 percent solids.

15. The method of claim 13 wherein the fatty acid salt is the salt of calcium, magnesium, barium, aluminum, or zinc.

16. The method of claim 13 wherein said higher fatty acid is selected from the group consisting of $C_{12}$ to $C_{22}$ fatty acids and mixtures thereof.

17. The method of claim 13 wherein the fatty acid salt is calcium stearate.

18. The method of claim 13 wherein the organic solvent is selected from the group consisting of benzene, toluene, xylene, mesitylene, 1,1,2-trichloroethane, and chloroform.

19. The method of claim 13 wherein said suture is composed of a polymer selected from the group consisting of homopolymers and copolymers of lactide and glycolide.

20. The method of claim 13 wherein said suture is composed of poly(p-dioxanone).

* * * * *